United States Patent [19]

Pearce et al.

[11] Patent Number: 5,789,604
[45] Date of Patent: Aug. 4, 1998

[54] ISOLATION, CHARACTERIZATION AND STRUCTURES OF NEW ANTIBIOTIC COMPONENTS PRODUCED BY FUNGAL CULTURE 07F275

[75] Inventors: Cedric John Pearce, Cornwall, N.Y.; Robert West, Seattle, Wash.; Gerhard Schlingmann, Hillburn, N.Y.

[73] Assignee: American Cyanamid Company, Wayne, N.J.

[21] Appl. No.: 60,072

[22] Filed: May 12, 1993

[51] Int. Cl.[6] .................................................. C07D 317/72
[52] U.S. Cl. ................................................ 549/336; 549/332
[58] Field of Search ........................... 549/332, 336, 549/333

[56] References Cited

FOREIGN PATENT DOCUMENTS 1-294686  11/1989  Japan.
326828    11/1989  Japan.

Primary Examiner—C. Warren Ivy
Assistant Examiner—Raymond Covington
Attorney, Agent, or Firm—Kenneth J. Dow

[57] ABSTRACT

New antibacterial agents produced by fungal culture 07F275, of which the compound designated 07F275 alpha having the following structure:

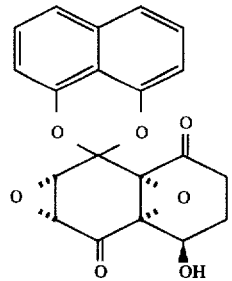

07F275alpha is representative. Methods for the fermentation, recovery and purification from crude solutions are also disclosed.

12 Claims, 10 Drawing Sheets

GENERAL UV FOR 07F275ALPHA, ZETA, SIGMA AND KAPPA $^1H$ NMR SPECTRUM OF 07F275SIGMA $CDCl_3$ SOLUTION $^1$H NMR SPECTRUM OF 07F275KAPPA IN $CD_3OD$ SOLUTION

X-RAY STRUCTURE OF 07F275KAPPA ns
5,789,604

ISOLATION, CHARACTERIZATION AND STRUCTURES OF NEW ANTIBIOTIC COMPONENTS PRODUCED BY FUNGAL CULTURE 07F275

SUMMARY OF THE INVENTION

This invention relates to new antibacterial agents produced by fungal culture 07F275, to their production by fermentation, to methods for their recovery and concentration from crude solutions and to processes for their purification. Isolation and purification of components produced by the culture has yielded antibacterial agents designated 07F275alpha, 07F275zeta, 07F275sigma and 07F275kappa as well as other minor components. The present invention includes within its scope the antibacterial agents in dilute form, as crude concentrates, as a complex of all components and in pure form as individual components. The effect of these new agents on specific microorganisms, together with their chemical and physical properties differentiate them from previously described antibacterial agents. These compounds are a novel class of antibiotics, distinguished by a spiro 1,8-naphthodioxane group which also give this family its characteristic chromophore.

DETAILED DESCRIPTION OF THE INVENTION

The antibacterial agents 07F275alpha, 07F275zeta, 07F275sigma and 07F275kappa, as well as other minor components, are produced by aerobic fermentation of fungal culture 07F275, originally isolated from a tree trunk in Parque National Soberania, Provincia de Panama, Panama. The culture was taxonomically characterized as a non-sporulating fungus by Dr. Barry Katz, MYCOsearch, Durham, N.C.

This fungus is maintained in the culture collection of the Medical Research Division, American Cyanamid Company, Pearl River, N.Y. as culture number 07F275. A viable culture of this new microorganism has been deposited with the ARS Culture Collection, Fermentation Laboratory, Northern Regional Research Center, U.S. Department of Agriculture, 1815 North University Street, Peoria, Ill. 61604 and has been added to its permanent collection. It has been assigned the strain designation NRRL 21081 by such depository. The fungus has been deposited under the Budapest Treaty.

Observations were made of the cultural and morphological features of culture 07F275 using methods well known in the art.

Comparative data on the morphology of 07F275 is given in Table 1.

07F275 was grown at 21° C. and 37° C. for 7 days on Yeast Extract Peptone Dextrose (YePD), Malt, Cornmeal, Potato Dextrose (PDA), and Czapek's agar media.

At 21° C. all colonies consisted of smooth-walled, acutely branched septate hyphae, 0.8–4.0 µm in diameter.

TABLE 1

| ISP Agar Medium | Color and Appearance of Culture |
| --- | --- |
| Yeast Extract Peptone Dextrose (YePD) | Colonies (7.8 mm dia.) were Light Olive Gray on surface and Blackish Dark Olive to Medium Buffy Brown on reverse, convex, densely felted with pronounced to slight radiate furrows and convolutions. A stroma of thicker-walled subglobose hyphae to 5 µm diameter diameter developed on surface. |
| Malt | Colonies (9.4 mm dia.) were Deep to Dark Olive on surface and reverse, zonate, tomentose to minutely tomentose. |
| Cornmeal | Colonies (9.0 mm dia) were Light Olive Gray on surface and Blackish Dark Olive to Medium Buffy Brown on reverse, convex, densely felted with pronounced to slight radiate furrows and convolutions. |
| Potato Dextrose (PDA) | Colonies (9.7 mm dia.) were Deep to Dark Olive on surface and reverse, zonate, tomentose to minutely tomentose. |
| Czapek's | Colonies (8.8 mm dia.) were Citrine Drab on surface and Dark Olive in reverse, zonate, tomentose to felted. |

Color names from P. Ridgway, "Color Standards and Nomenclature", Washington, D.C., 1912.

There was no growth in any medium at 37° C. The colonies had no odor.

A total of twelve components were isolated by Chromatography as shown in Graph 1.

The physicochemical characteristics of the major components are as follows:

07F275alpha a) Apparent Molecular Formula: $C_{20}H_{14}O_7$ b) Molecular Weight: MS(FAB) [M+H]=M/Z 367

HRMS calcd. for $C_{20}H_{14}O_7$=M/Z 366.0740

Figure 1:
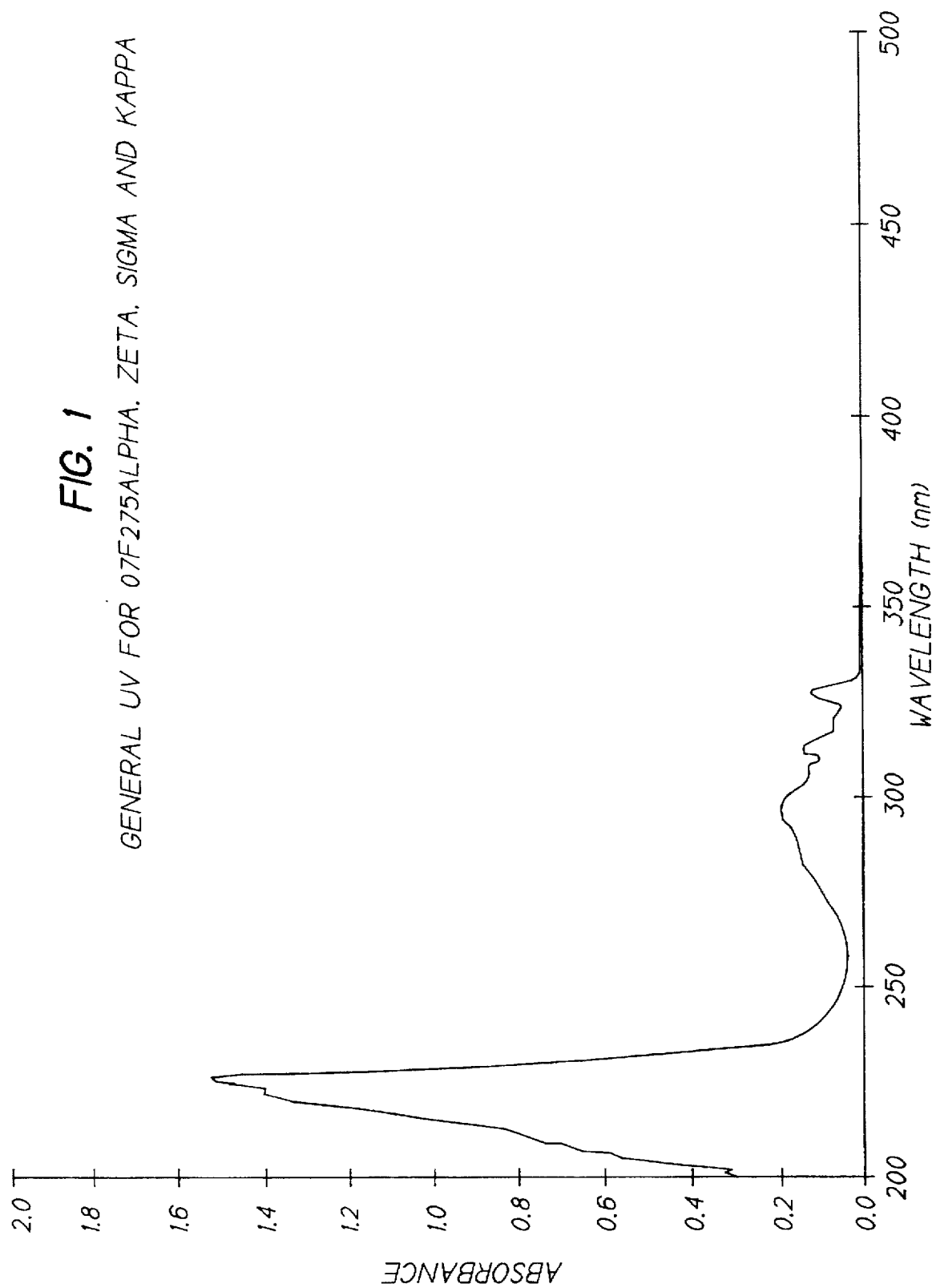
FIG. 1 shows a general ultraviolet absorption spectrum for 07F275alpha, 07F275zeta, 07F275sigma and 07F275kappa.
Figure 2:
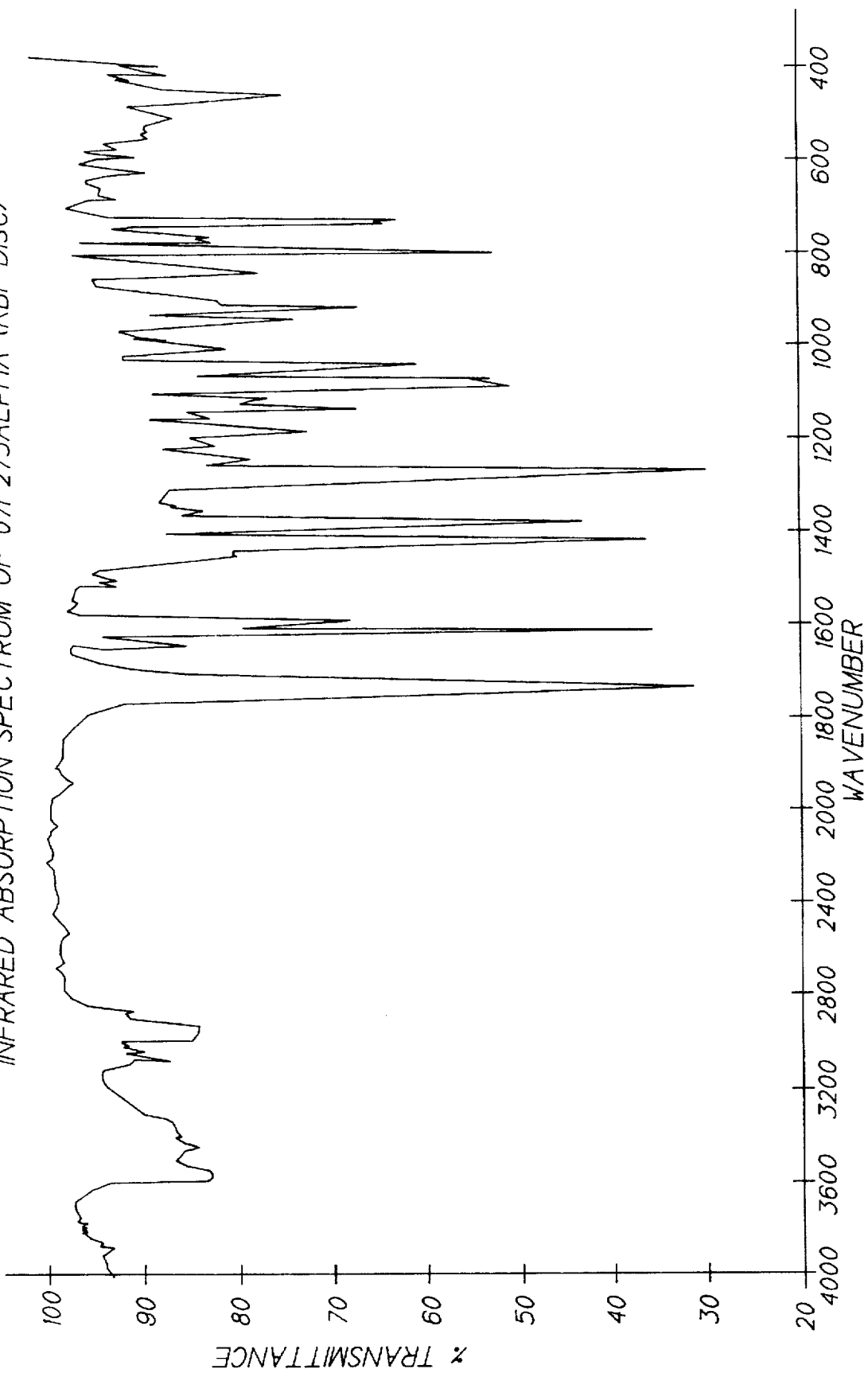
FIG. 2 shows an infrared spectrum for 07F275alpha.
Figure 3:
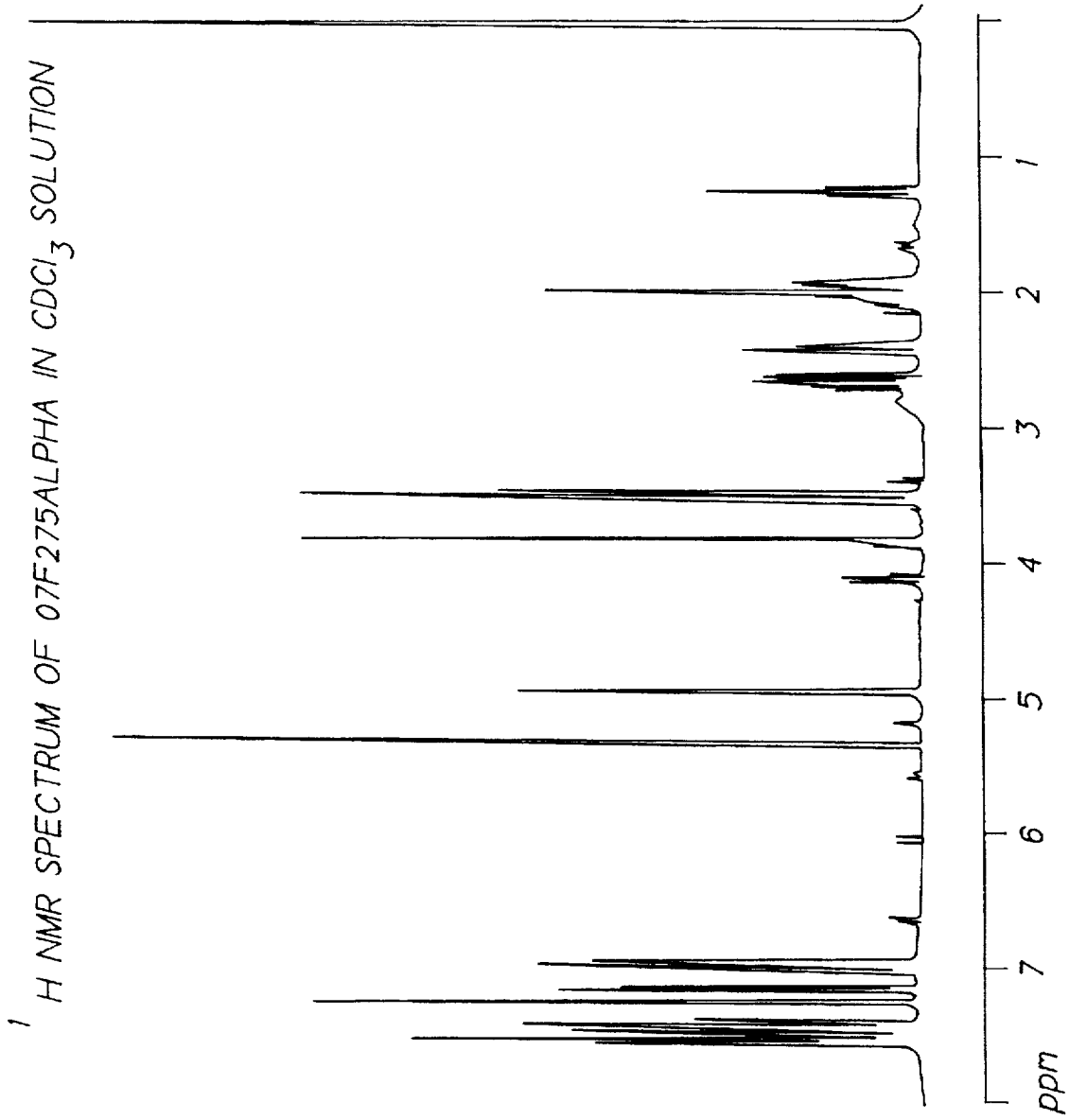
FIG. 3 shows a H NMR spectrum for 07F275alpha.
Figure 4:
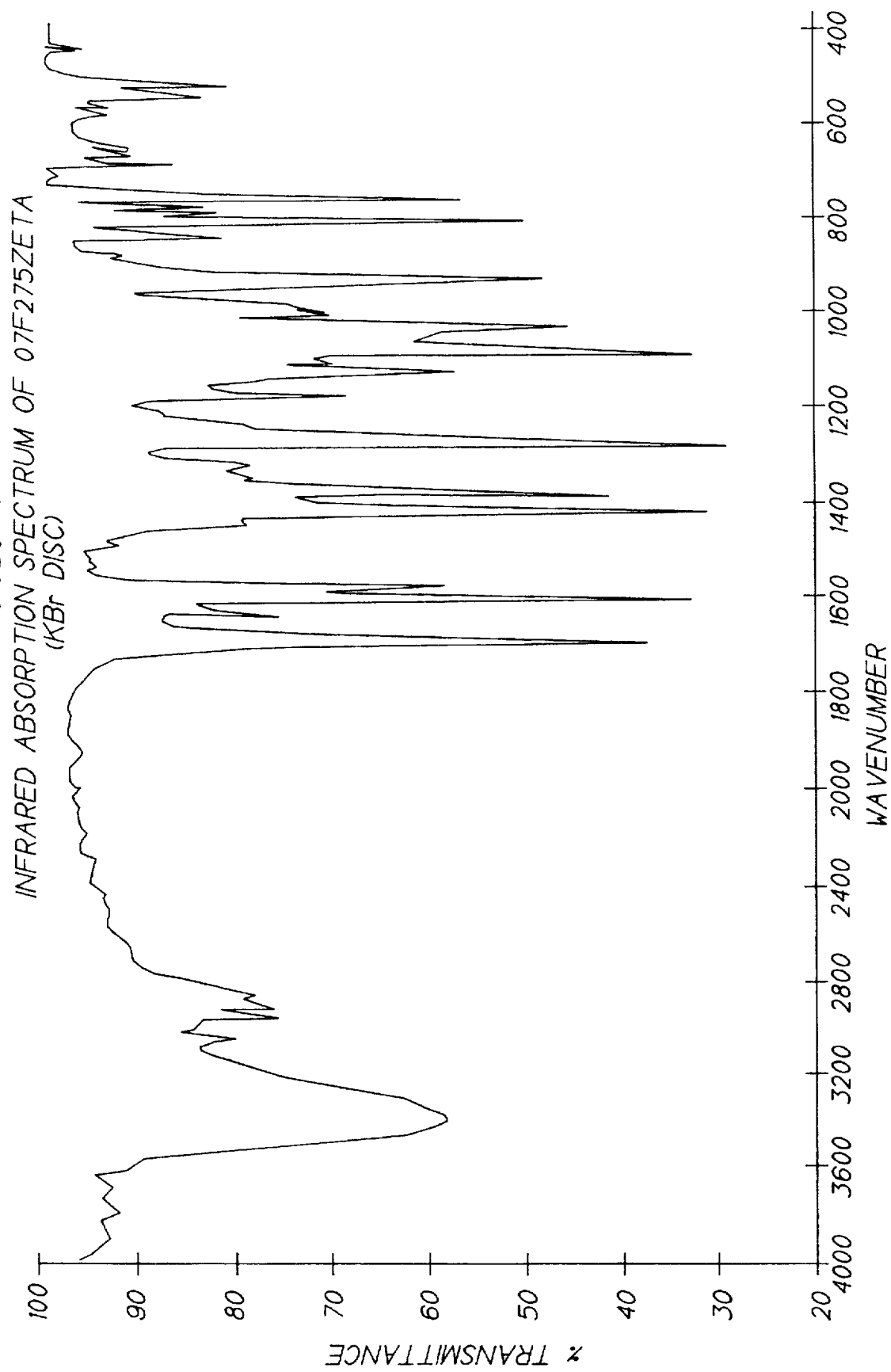
FIG. 4 shows an infrared spectrum for 07F275zeta.

HRMS observed=M/Z 366.0738 c) Specific Rotation: $[\alpha]_D^{25}$+30±16, conc. 0.183%, $CH_3OH$ d) Ultraviolet Absorption Spectra: as shown in FIG. 1; kmax nm e ETOH=226 (60,000), 298 (8,000), 314 (5,890), 328 (5,000);

f) Infrared Absorption Spectrum: as shown in FIG. 2 (KBr disk): 3482, 3431, 3024, 2944, 2871, 1721(s), 1610(s), 1586(s), 1443, 1413(s), 1380(s), 1274(s), 1237, 1182, 1138, 1088, 1038, 951, 922, 858, 819, 753 cm$^{-1}$;

g) Proton Magnetic Resonance Spectrum: as shown in FIG. 3 (300 MHz, $CDCl_3$);

h) Carbon-13 Nuclear Magnetic Resonance Spectrum: (300 MHz, $CDCl_3$, ppm downfield from TMS), significant peaks are listed below:

| | | | |
| --- | --- | --- | --- |
| 197.8 | 127.7 | 109.9 | 62.6 |
| 194.9 | 127.3 | 109.2 | 58.0 |

| | | | |
|---|---|---|---|
| 144.9 | 121.4 | 93.7 | 54.9 |
| 144.9 | 121.2 | 67.9 | 32.3 |
| 134.1 | 111.9 | 66.1 | 22.4 |

Figure 5:
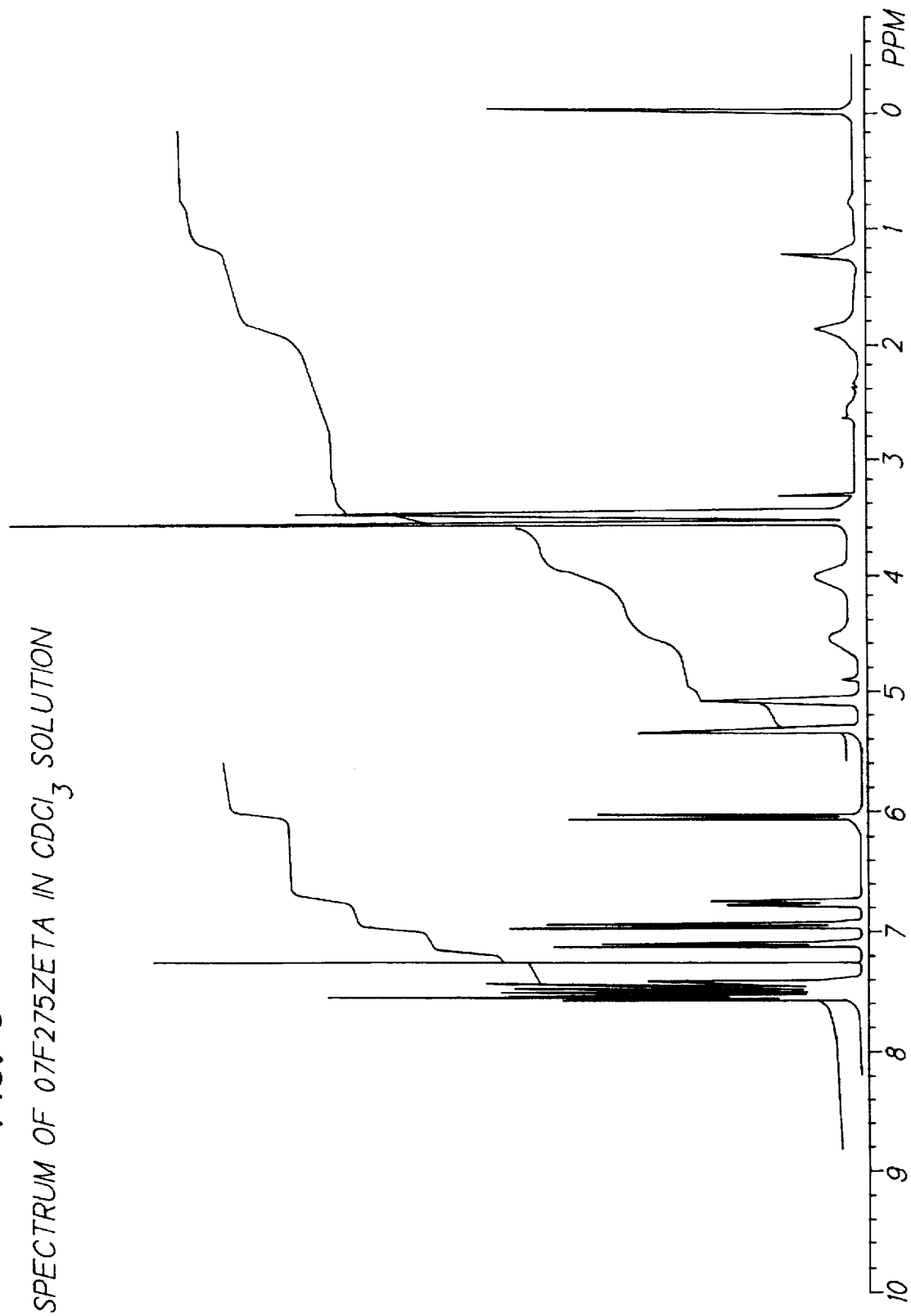
FIG. 5 shows a H NMR spectrum for 07F275zeta.
Figure 6:
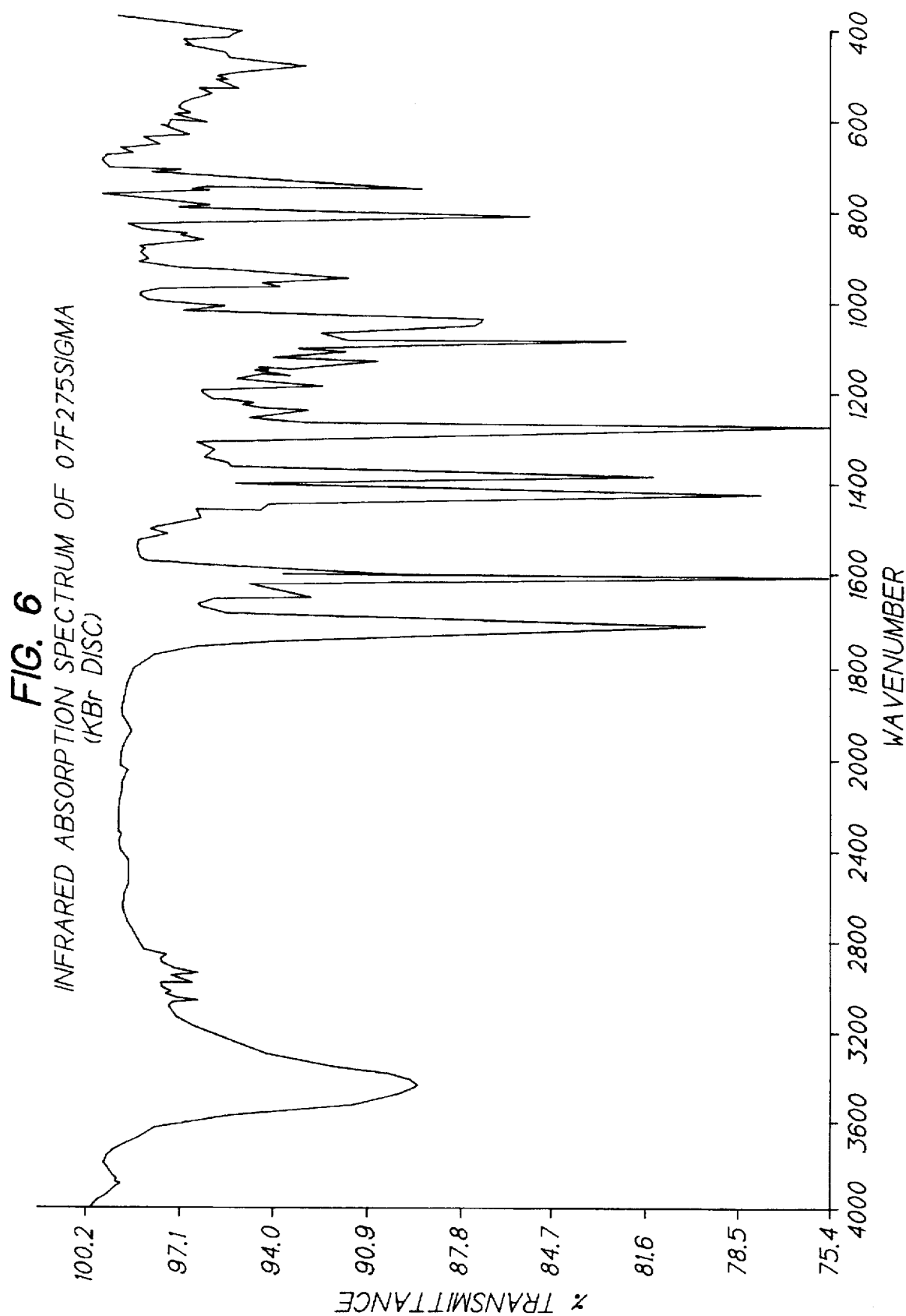
FIG. 6 shows an infrared spectrum for 07F275sigma.

07F275zeta a) Apparent Molecular Formula: $C_{20}H_{14}O_7$ b) Molecular Weight: MS(nTSP) $|M|^-$=M/Z 366; MS(FAB) |M+H|=M/Z 367;

HRMS calcd. for $C_{20}H_{14}O_7$=M/Z 366.0739
HRMS observed=M/Z 366.0738 c) Specific Rotation: $|\alpha|_D^{25}$+75±8, conc. 0.3%, $CH_3OH$ d) Ultraviolet Absorption Spectra: as shown in FIG. 1; kmax nm e $CH_3OH$=226 (61,800), 299 (8,000), 313 (5,900), 328 (4,800);

e) Infrared Absorption Spectrum: as shown in FIG. 5 (KBr disk): 3418(br), 2944, 2924, 2853, 1695(s), 1609(s), 1586 (s), 1414(s), 1381(s), 1276(s), 1087, 1182, 1138, 1118, 1091, 1036, 947, 819, 757cm$^{-1}$;

f) Proton Magnetic Resonance Spectrum: as shown in FIG. 5 (300 MHz, CDCl or $CH_3OD$);

g) Carbon-13 Nuclear Magnetic Resonance Spectrum: (300 MHz, $CDCl_3$, ppm downfiled from TMS), significant peaks are listed below:

| | | | |
|---|---|---|---|
| 187.3 | 127.7 | 112.0 | 63.2 |
| 145.3 | 127.3 | 109.7 | 61.4 |
| 145.0 | 126.6 | 108.9 | 61.4 |
| 142.7 | 121.1 | 94.4 | 55.6 |
| 134.1 | 121.0 | 70.8 | 54.4 |

Figure 7:
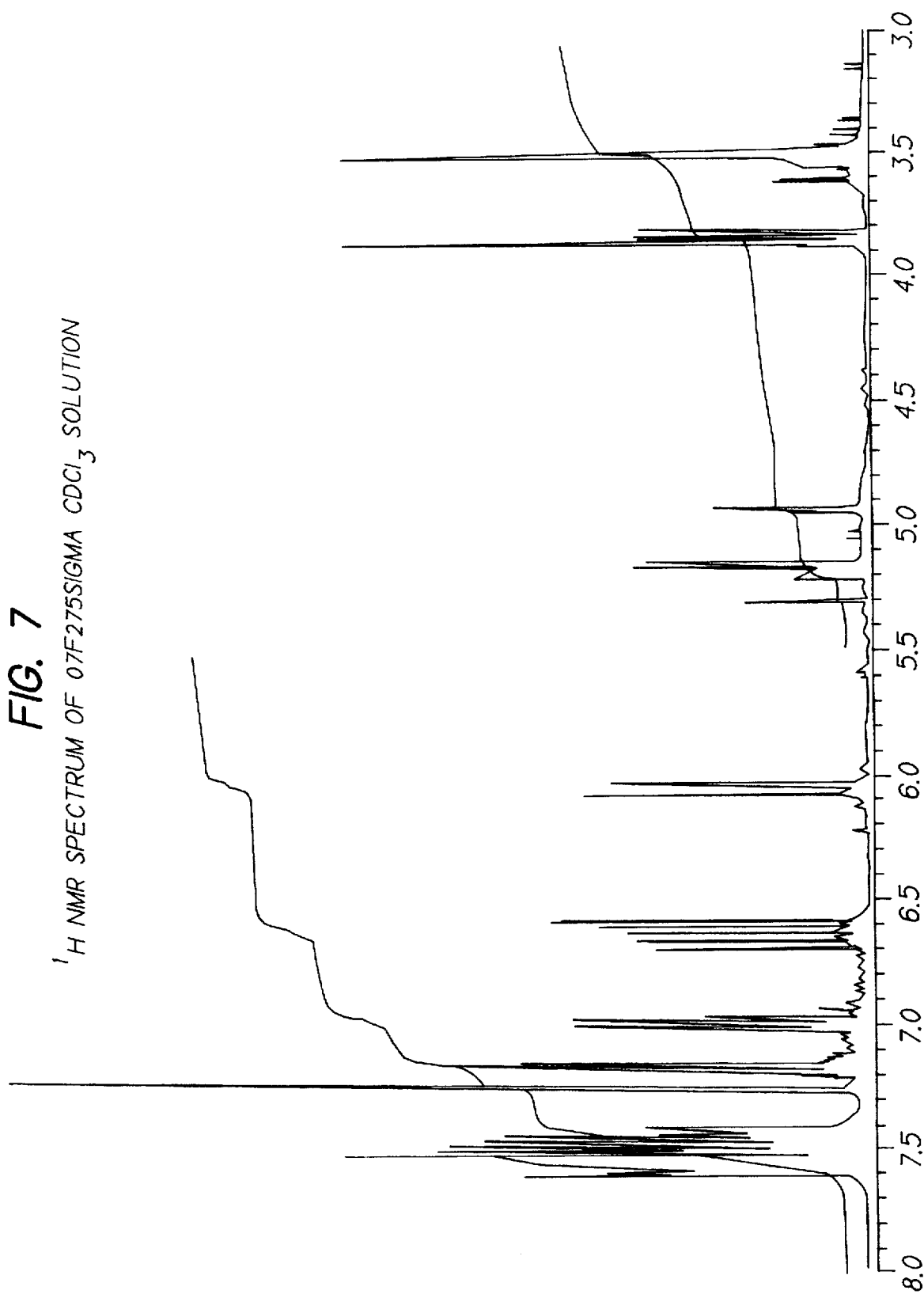
FIG. 7 shows a H NMR spectrum for 07F275sigma.
Figure 8:
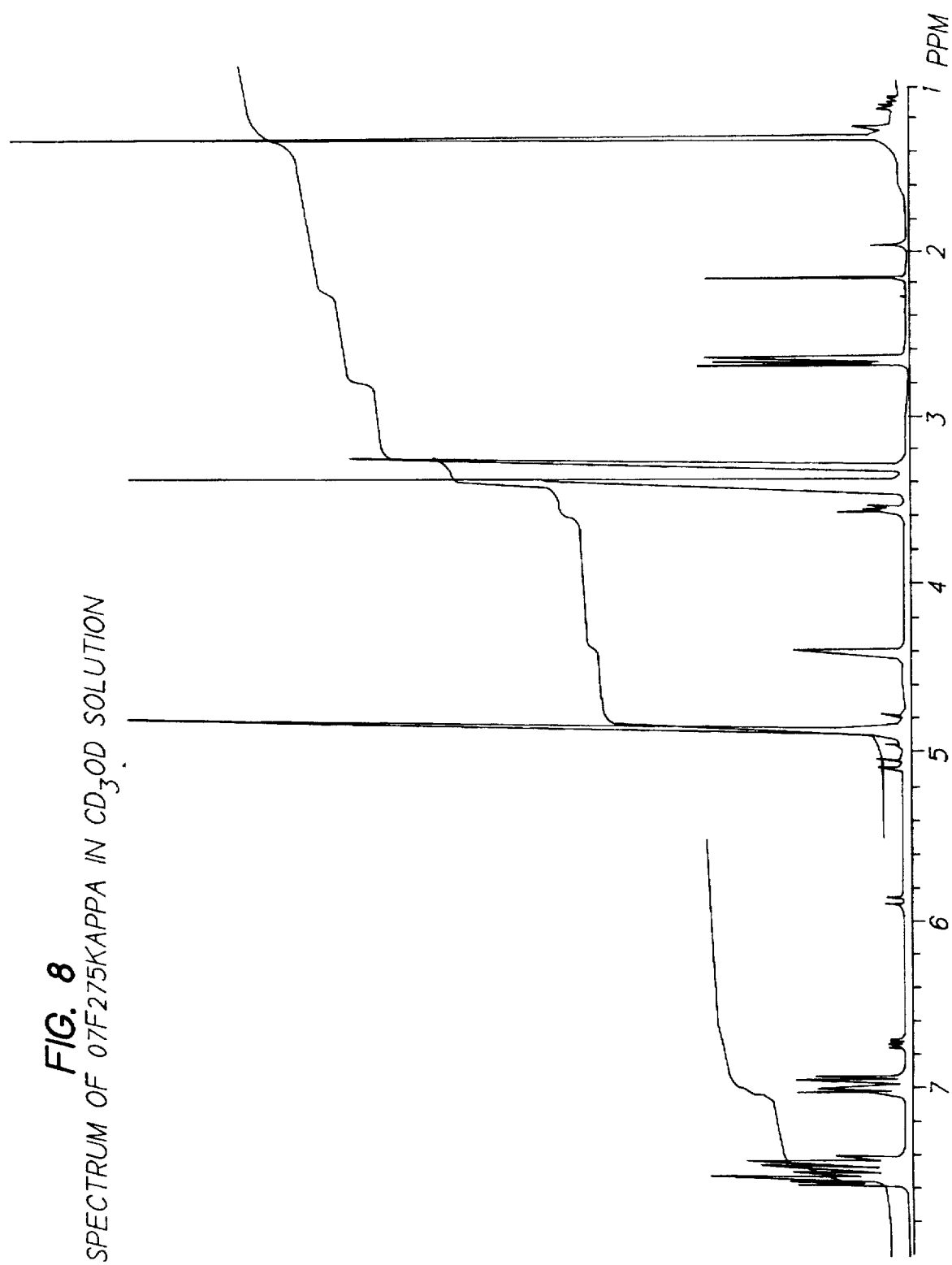
FIG. 8 shows a H NMR spectrum for 07F275kappa.

07F725sigma a) Apparent Molecular Formula: $C_{20}H_{12}O_7$ b) Molecular Weight: MS(nTSP) $[M]^-$=M/z 364;

c) Specific Rotation: $[\alpha]_D^{25}$+67±8, conc. 0.3%, $CH_3OH$ d) Ultraviolet Absorption Spectra: as shown in FIG. 1; kmax nm e $CH_3OH$=226 (62,100), 299 (8.00), 313 (5,900), 328 (4,800);

e) Infrared Absorption Spectrum: as shown in FIG. 8 (KBr disk): 3484(br), 2946, 2924, 1725(s), 1695(s), 1609(s), 1586(s), 1413, 1380, 1273, 1087, 1038, 951, 922, 818, 752cm$^{-1}$;

f) Proton Magnetic Resonance Spectrum: as shown in FIG. 7;

g) Carbon-13 Nuclear Magnetic Resonance Spectrum: (300 MHz, $CD_3OD$, ppm downfiled from TMS), significant peaks are listed below:

| | | | |
|---|---|---|---|
| 197.6 | 134.1 | 120.3 | 66.3 |
| 185.4 | 127.8 | 111.9 | 65.4 |
| 144.9 | 127.8 | 109.9 | 61.9 |
| 144.9 | 127.4 | 109.2 | 58.0 |
| 139.8 | 121.4 | 93.5 | 54.6 |

Figure 9:
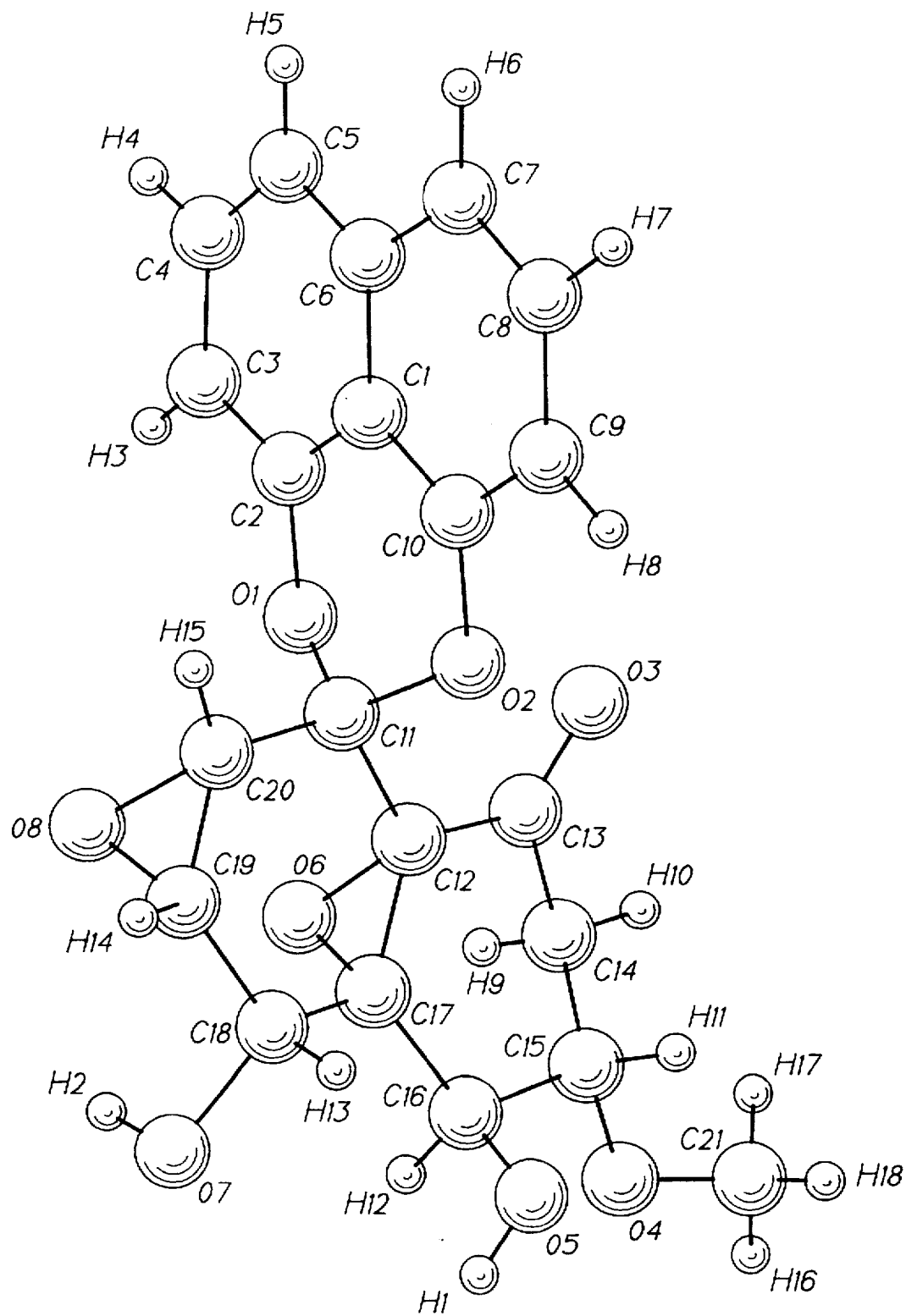
FIG. 9 shows an X-ray structure for 07F275kappa.
Figure 10:
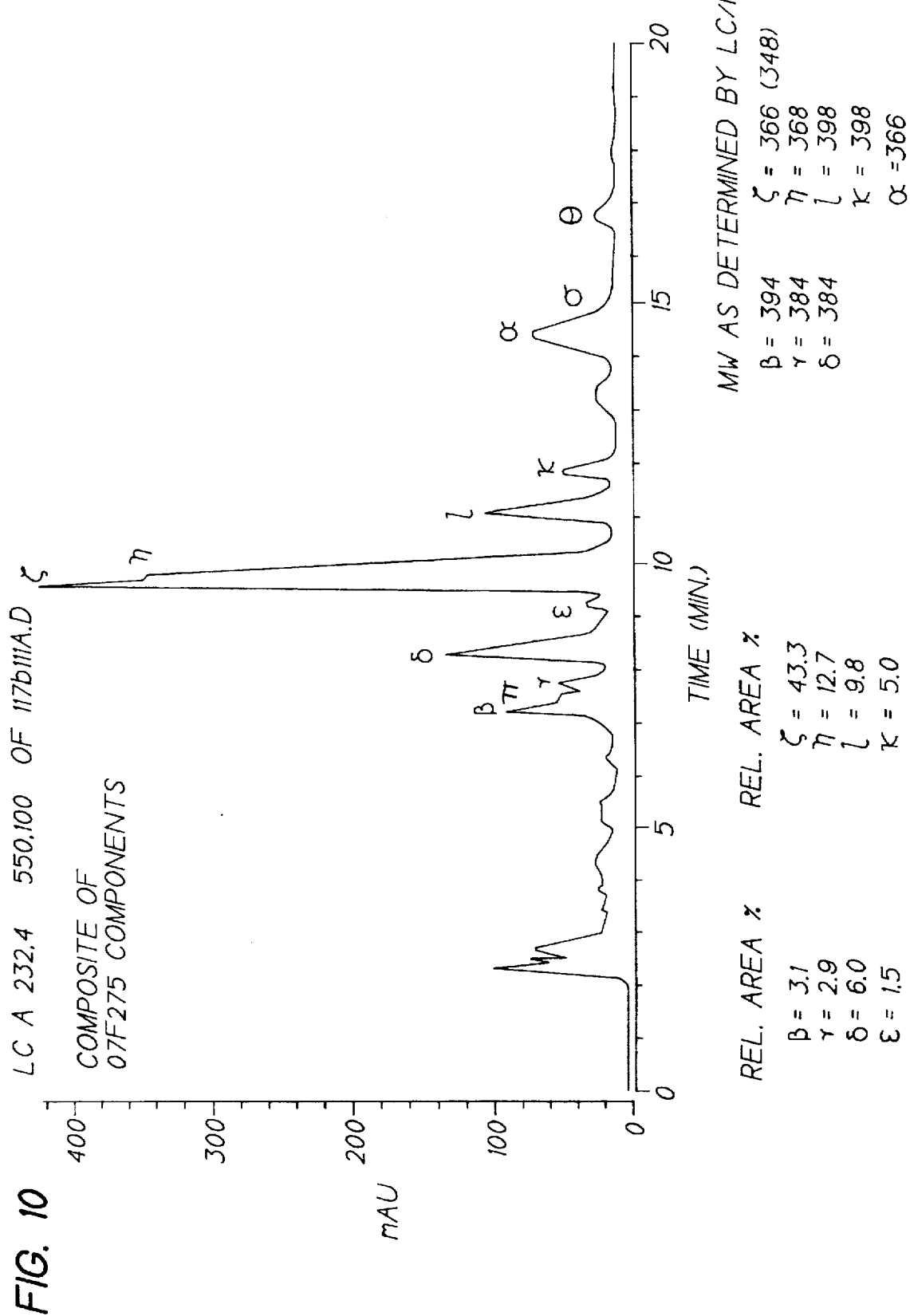
FIG. 10 shows the composite chromatographic spectrum of the twelve components produced by the 07F275 culture.

07F275kappa a) Apparent Molecular Formula: $C_{21}H_{18}O_8$ b) Molecular Weight: MS(nTSP) $|M|^-$=M/z 398;

c) Ultraviolet Absorption Spectra: as shown in FIG. 1; $\lambda$max nm $\epsilon$ $CH_3OH$=226 (59,230), 299 (8,000), 313 (5,900), 328 (4,800);

d) Proton Magnetic Resonance Spectrum: as shown in FIG. 8;

e) Carbon-13 Nuclear Magnetic Resonance Spectrum: (300 MHz, $CD_3OD$, ppm downfield from TMS), significant peaks are listed below:

| | | | |
|---|---|---|---|
| 199.2 | 128.5 | 109.8 | 65.0 |
| 147.2 | 122.0 | 96.6 | 63.4 |
| 146.9 | 121.9 | 81.5 | 57.6 |
| 135.7 | 113.4 | 71.4 | 54.5 |
| 128.7 | 110.3 | 67.0 | 40.7 | f) Melting Point: crystal (MeOH); 158° C., resolidifies then melts 232° C.;

g) X-ray Structure: as shown in FIG. 9;

Structures were assigned on the basis of spectroscopic data obtained, particularly those from 1D and 2D NMR experiments, and correlated with the structure of 07F275kappa which was determined by single crystal X-ray diffraction. Components 07F275zeta, 07F275eta, and their oxidized forms 07P275sigma, and 07F275alpha are considered to be natural forms. Component pairs 07F275gamma, 07F275delta and 07F275iota and 07F275kappa are considered to be artifacts of 07F275zeta, formed during the fermentation and isolation procedures.

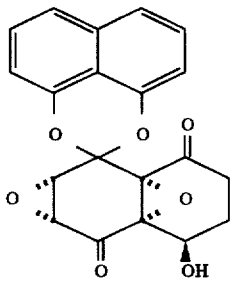

07F275alpha

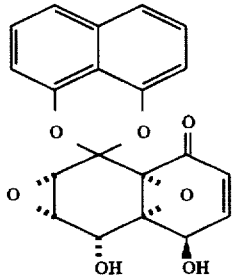

07F275zeta

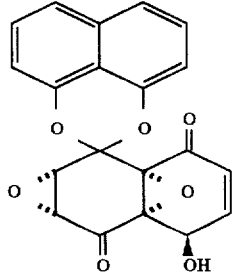

07F275sigma

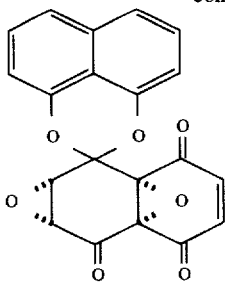

07F275theta

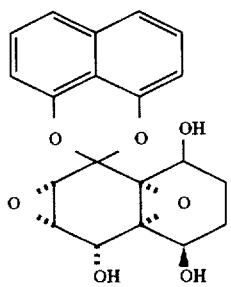

07F275epsilon

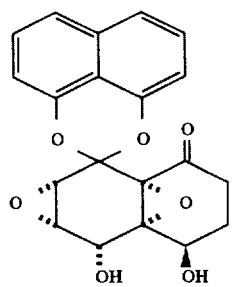

07F275eta

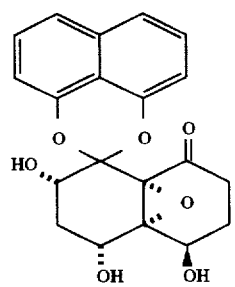

07F275pi

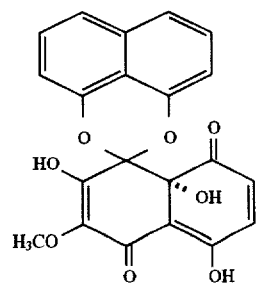

07F275beta

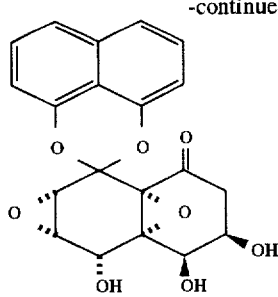

07F275gamma

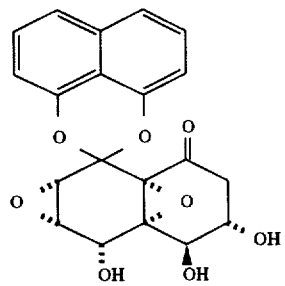

07F275delta

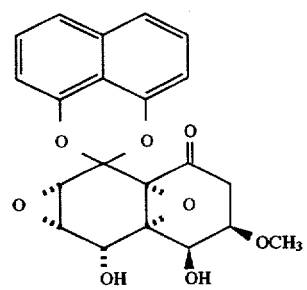

07F275Iota

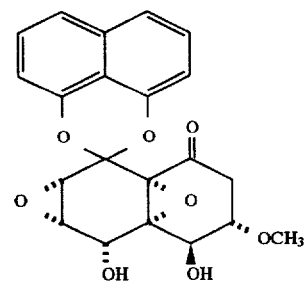

07F275kappa

It is to be understood that for the production of the new antibacterial agents 07F275alpha, 07275zeta, 07275kappa and 07275sigma, the present invention is not limited to this particular organism or to organisms fully answering the above growth and microscopic characteristics, which are given for illustrative purposes only. In fact, it is desired and intended to include the use of mutants produced from this organism by various means such as exposure to x-radiation, ultraviolet radiation, N'-methyl-N-nitro-N-nitrosoguanidine and the like.

BIOLOGICAL ACTIVITY
in Vitro Antibacterial Screen (Table 1)

The in vitro antibacterial effects of antibiotics 07P275alpha, 07275zeta, 07275sigma and 07275kappa were determined by standard agar dilution methods against clinical isolates obtained from medical centers representing various geographical areas in the United States. The inoculum of each culture was approximately 1 to $5 \times 10^4$ colony forming units applied with a steers multiple inocula replicator to plates containing the antibiotic in Mueller-Hinton agar. The agar was supplemented with about 5% sheep blood where required for the growth of the organism. The results are given in Table 1.

in Vivo Evaluation as Fungicidal Agents (Table 2)

Compounds are dissolved in acetone, diluted to the desired concentration with water and surfactant and sprayed onto the test plants. After drying, the test plants are treated with fungal inoculum. When disease symptom development is optimal, plants are rated for disease control. Inoculated untreated plants, solvent/surfactant treated plants and plants treated with a reference standard are used for comparison.

| HEADER | COMMON NAME | SCIENTIFIC NAME |
|---|---|---|
| AS | Apple scab | Venturia inaequalis |
| GDM | Grape downy mildew | Plasmopara viticola |
| PB | Pepper botrytis | Botrytis cinerea |
| RB | Rice blast | Pyricularia oryzae |
| SBC | Sugar beet cercospora | Cercospora beticola |
| TEB | Tomato early blight | Alternaria solani |
| WSN | Wheat septoria nodorum | Leptosphaeria nodurum |
| WPM | Wheat powdery mildew | Erysiphe graminis f.sp. tritici |

Compounds are rated for control of each disease according to the rating scale shown below:

| Rating | % Control of Disease |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

The results are reported in Table 2.

in Vitro Evaluation of the Inhibition of the Mycelial Growth by Target (Table 3)

Severe soilborne diseases such as damping off, seedling blight, crown rot, and root rot, among others are caused by certain plant pathogenic fungi. An in Vitro assay is conducted to determine whether test compounds will inhibit the mycelial growth of said fungi. Pathogens, the method of testing, and the rating system used are reported below.

General Procedure for the in Vitro Fungicide Screen Assay fungi included the following plant pathogens: FUSOXC *Fusarium oxysporum* Schlechtend: Fr.f.sp. cucumerinim J. H. Owen PSDCHE *Psudocercosporella herpotrichoides* Deighton
PYTHUL *Pythium ultimam* Trow
RHIZSO *Rhizoctonia solani* Kuehn AG1 1A The test compound (2.5–10 mg) is dissolved in 0.5 ml acetone, diluted with 4.5 ml sterile deionized water, and mixed with 95 ml of an autoclaved and partially cooled, chemically defined agar medium in a 250 ml flask. Test compounds that are insoluble are prepared as a fine suspension ultrasonically or with a glass tissue grinder, before addition to the medium. The chemically defined medium (CDM) used in these experiments is as follows:

| | |
|---|---|
| Sucrose | 15.00 g |
| $NH_4Cl$ | 0.50 g |
| $KNO_3$ | 0.50 g |
| $KH_2PO_4$ | 0.50 g |
| $K_2HPO_4$ | 0.50 g |
| $MgSO_4.7H_2O$ | 0.25 g |
| Micronutrient Stock Solution (add after water) | 10 ml |
| Water (deionized) | 990.0 ml |

CDM is sterilized by autoclaving or by filtration through a 0.22 mort time period and used in other concentration of the solution is 9 ml/ml (9000. ppm).

The mixture of test compound and agar medium as described above is poured into several 100 mm×15 mm sterile plastic plates and allowed to solidify. The surface of each plate is inoculated with a single disc of mycelium and agar cut with an 8 mm diameter cork borer from actively growing cultures of assay fungi on a chemically defined agar medium. The plates are incubated at room temperature. Growth inhibition is determined when the mycelial growth on unamended control media has reached the edge of the petri plates. The time interval varies depending on the growth rate of the fungus. Each colony diameter is measured and compared with the untreated control and the percent inhibition is calculated as follows:

$$\% \text{ Mycelial growth inhibition} = \frac{\text{Growth of untreated control (mm) minus the Growth of treatment (mm)}}{\text{Growth of untreated control (mm)}} \times 100$$

Each test includes a solvent blank consisting of the formulation without a test compound in addition to the untreated control.

The data obtained are shown in Table 3.

TABLE 1

| | Antibacterial Activity MIC (g/ml) | | | | | | | |
|---|---|---|---|---|---|---|---|---|
| Organisms | CONTROL Piperacillin | CONTROL Vancomycin | CONTROL Erythromycin | 07F275 zeta | 07F275 eta | 07F275 sigma | 07F275 alpha | Prep B (crude mix) |
| 1. *S. aureus*(MEMC-89-4) | >128.000 | 1.000 | >128.000 | 8.000 | >32.000 | 8.000 | 16.000 | NT |
| 2. *S. aureus*(ID-2371) | >128.000 | 1.000 | >128.000 | 16.000 | >32.000 | 8.000 | 8.000 | NT |
| 3. *S. aureus*(ID-2727) | 128.000 | 1.000 | 4.000 | 16.000 | >32.000 | 8.000 | 8.000 | NT |
| 4. *S. aureus*(SMITH) | 1.000 | 1.000 | 0.250 | 8.000 | >32.000 | 8.000 | 16.000 | 16.00 |
| 5. *S. aureus*(ID-3105) | 2.000 | 1.000 | >128.000 | 8.000 | >32.000 | 8.000 | 8.000 | NT |
| 6. *S. aureus*(ID-4379) | 4.000 | 1.000 | 64.000 | 16.000 | >32.000 | 8.000 | 16.000 | NT |

TABLE 1-continued

Antibacterial Activity MIC (g/ml)

| Organisms | CONTROL Piperacillin | CONTROL Vancomycin | CONTROL Erythromycin | 07F275 zeta | 07F275 eta | 07F275 sigma | 07F275 alpha | Prep B (crude mix) |
|---|---|---|---|---|---|---|---|---|
| 7. S. aureus(ATCC 29213) | 2.000 | 1.000 | 0.500 | 16.000 | >32.000 | 8.000 | 16.000 | 8.00 |
| 8. S. hemolyticus(ID-4061) | >128.000 | 1.000 | >128.000 | 16.000 | >32.000 | 16.000 | 8.000 | NT |
| 9. SCN(ID-3135) | >128.000 | 4.000 | >128.000 | 16.000 | >32.000 | 16.000 | 8.000 | NT |
| 10. SCN(ID-3276) | 8.000 | 2.000 | 0.120 | 16.000 | >32.000 | 8.000 | 8.000 | NT |
| 11. SCN(ID-3120) | 16.000 | 1.000 | >128.000 | 16.000 | >32.000 | 8.000 | 4.000 | NT |
| 12. SCN(ID-3941) | 2.000 | 1.000 | 64.000 | 16.000 | >32.000 | 8.000 | 8.000 | NT |
| 13. SCN(4615) | 1.000 | 2.000 | 0.250 | 16.000 | >32.000 | 4.000 | 8.000 | NT |
| 14. E. faecalis(ID-4168) | 2.000 | 1.000 | 2.000 | 16.000 | >32.000 | 16.000 | 16.000 | NT |
| 15. E. faecalis(ID-1829) | >128.000 | 0.500 | >128.000 | 32.000 | >32.000 | 16.000 | >32.000 | NT |
| 16. E. faecalis(ID-2131) | 2.000 | 1.000 | 16.000 | 16.000 | >32.000 | 16.000 | 16.000 | NT |
| 17. E. faecalis(12201) | 8.000 | >128.000 | >128.000 | 16.000 | >32.000 | 16.000 | 8.000 | NT |
| 18. E. faecalis(ATCC 29212) | 2.000 | 2.000 | 2.000 | 32.000 | >32.000 | 16.000 | 8.000 | NT |
| 19. E. faecium(12202) | >128.000 | >128.000 | >128.000 | 32.000 | >32.000 | 16.000 | >32.000 | NT |
| 20. E. faecium(ID-3301) | 2.000 | 1.000 | >128.000 | 16.000 | >32.000 | 16.000 | 16.000 | NT |
| 21. E. faecium(ID-4133) | 0.120 | 0.500 | <=0.060 | 32.000 | >32.000 | 32.000 | 32.000 | NT |
| 22. E. avium(ID-3953) | >128.000 | >128.000 | >128.000 | 32.000 | >32.000 | 16.000 | >32.000 | NT |
| 23. S. pyogenes(ID-3187) | <=0.060 | 0.500 | <=0.060 | 8.000 | >32.000 | 16.000 | 16.000 | NT |
| 24. S. agalactiae(ID-4079) | 0.120 | 1.000 | 0.120 | 16.000 | >32.000 | >32.000 | 16.000 | NT |
| 25. S. pneumo(ID-4444) | <=0.060 | 1.000 | <=0.060 | 8.000 | >32.000 | 8.000 | 8.000 | NT |
| 26. P. aeruginosa(ATCC 27853) | 2.000 | >128.000 | >128.000 | >32.000 | >32.000 | >32.000 | >32.000 | NT |
| 27. M. morganii(VGH 84-11) | 64.000 | >128.000 | >128.000 | >32.000 | >32.000 | >32.000 | >32.000 | NT |
| 28. E. coli(J2175) | 1.000 | >128.000 | 128.000 | >32.000 | >32.000 | >32.000 | >32.000 | >128.00 |
| 29. E. coli(J2445) | <=0.060 | 0.500 | <=0.060 | 32.000 | >32.000 | 32.000 | 16.000 | >4.00 |
| 30. E. coli(ATCC 25922) | 2.000 | >128.000 | 64.000 | >32.000 | >32.000 | >32.000 | >32.000 | >128.00 |
| 31. B. cereus(Bacto) | 2.000 | 1.000 | 0.120 | 8.000 | >32.000 | 8.000 | 8.000 | 16.00 |
| 32. S. lutea(ATCC 9341) | <=0.060 | 0.500 | <=0.060 | 4.000 | >32.000 | 4.000 | 16.000 | NT |

NT = Not Tested

TABLE 2

IN VIVO SCREENING DATA:
DISEASE CONTROL BY TARGET

| CPD | DOSE (ppm) | AS | GDM | PB | RB | SBC | TEB | WPM | WSN |
|---|---|---|---|---|---|---|---|---|---|
| 07F275 sigma | 200.0 | 0 | 6 | 0 | 6 | 0 | 0 | 0 | 0 |
| | 50.0 | 0 | 4 | 0 | 2 | 0 | 0 | 0 | 0 |
| | 12.5 | 0 | 0 | 0 | 0 | 0 | 0 | 0 | 0 |

TABLE 3

IN VITRO SCREENING DATA:
MYCELIAL INHIBITION BY TARGET

| CPD | DOSE (ppm) | FUSOXC | PSDCHE | PYTHUL | RHIZSO |
|---|---|---|---|---|---|
| 07F275 sigma | 25.0 | 0 | 1 | 7 | 1 |
| | 10.0 | 0 | 1 | 7 | 1 |
| | 1.0 | 0 | 1 | 3 | 1 |

07F275sigma is active against Pythium at 10 ppm, but not at lower dosages. Little or no activity is found against other fungi in vitro. In greenhouse test 07F275sigma reduces the severity of two diseases, GDM and RB by about 85% using a dosage of 200 ppm. Little to no control is observed at lower dosages.

The products according to the invention which have good antimicrobial activity can be used in pharmaceutical, disinfectant, cosmetic or food preparations, especially as antiseptics by local and general application, as disinfectants and as preservatives.

As antiseptics for human or veterinary use, the concentration of active product can vary from 0.01% to 5% according to the use and the chosen formulation. Thus, it is possible to prepare foaming detergent solutions to be used by surgeons and nursing staff for washing their hands or to used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing products according to the invention are obtained as amphoteric, anionic, cationic or non-ionic surfactants at a concentration of 0.3 to 30%, humectants, such as glycols or polyethylene glycols, at a concentration of 0 to 20%, ethylene oxide and polypropylene copolymers at a concentration of 0 to 20%, and an alcohol (ethyl alcohol, isopropyl alcohol, benzyl alcohol) or a polyol, such as glycerol, at a concentration of 0 to 15%, as well as agents for complexing $Ca^{++}$, $Mg^{++}$ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

If the product according to the invention has a poor solubility in water, it is possible to use microemulsions, micellar solutions or other phase of the ternary or quaternary diagram of water/active principle/surfactant/co-surfactant which permits solubilization in water. These solutions can be used in diluted or undiluted form and can be dispensed for example by means of a vasopump or liquefied or non-liquefied propellants.

With the same constituents at appropriate concentrations, the products according to the invention can also be used to prepare simple aqueous solutions or aqueous solution in the form of sprays for making operative field antiseptic, for post operative treatment, for the treatment of burns, superinfected eczema, gluteal erythema, wounds or acne or for deodorants.

Simple alcoholic solutions or alcoholic solutions in the form of sprays containing 20 to 80% of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). The solutions are to be used for making the skin antiseptic febore puncture, for preparing the operative field, by nursing staff for making their hands antiseptic and for treating closed infected dermatosis, folliculitis, perionychia or acne.

The product according to the invention can be applied in the form of creams which contain some of the compounds mentioned for the preparation of solutions, together with the fatty substances normally found in the preparation of creams or emulsions. These creams can be used especially for the prevention of superinfections of gluteal erythema, eczema, mycosis or acne.

The products according to the invention may be used in eye lotions, eye solutions or ophthalmic ointment for treating eye infections (for example blepharitis or conjunctivitis), or in liquids for rinsing contact lenses. These forms for the eyes can be prepared using the same constituents as those used for the solution, care being taken to ensure that the mixture is isotonic.

The products according to the invention can also be used in animals for indications such as the prevention or treatment of infected lesions or lesions liable to become superinfected. In this case, the pharmaceutical compositions are similar to those used in man, in particular creams, sprays or solutions.

Moreover, the rapid lethal action on germs of the products according to the invention enable them to be used as surface disinfectants at concentrations which can vary from 0.1 to 4%. In this case, the products are used in preparations such as aqueous or non-aqueous foaming detergent solutions, sprays or nebulizers. Preparations of this type are particularly useful in the hospital or veterinary sectors, for local communities or agrifoodstuff industries. These preparations can contain the same constituents as those used in the antiseptic formulation, although a variety or organic solvents may be added.

In therapeutic use, the compound of this invention may be administered in the form of conventional antimicrobial pharmaceutical compositions appropriate for the intended use.

The antifungal compounds of the present invention are effective for controlling and/or preventing phytopathogenic fungi when employed in effective amounts. This will vary somewhat with the virility of the fungus in question and with other factors such as the environment in which treatment is conducted. These compounds are especially useful for the control of fungi which are the causative agents for grape downy mildew and potato and tomato late blight. Certain compounds of the invention may not only be employed to control fungi that has infected the plants, but also may be applied to healthy plants or seeds or to the soil in which the plant is to be grown in order to prevent infestation.

To protect plants from phytopathogenic fungi, the compounds of formula I are applied to the foliage of the plant, to the seed of the plants, or to the soil in which the plant grows or is to be grown, in the form of a liquid, preferably an aqueous spray, or dust, or granular formulation. Solutions or suspensions containing from about 20 ppm to about 1,000 ppm, and preferably 50 ppm to 500 ppm, of formula I compounds are generally effective for this use.

The compounds of the invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with inert, pharmacologically acceptable solid or liquid diluents.

For example, wettable powders, dusts, and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical flowable liquid can be prepared by admixing about 30% to 90% by weight of the active ingredient with about 1% to 3% by weight of a gelling agent such as bentonite, 2% to 5% by weight of a dispersing agent such as sodium lignosulfonate, about 1% by weight of polyethyleneglycol, and about 40% to 60% by weight of water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

Application of the material is made by adding a predetermined quantity of formulated product, such as described above, to the desired volume of water or other suitable solvent, alone or in combination with other agronomic chemicals for simultaneous use.

It is understood that the compounds of the present invention can be applied singly or in combination with one or more other fungicidal compounds, such application being made either by combination of the fungicidal compounds or their formulations in a common container prior to use or by sequential application of the active fungicidal compounds or their formulations to the host crop or its environment. Compounds suitable for combination with the compounds of this invention are suggested by, but not limited to, the following: 4,6-dinitro-o-cresol, benalaxyl, benomyl, captafol, captan, carbendazim, chlorothalonil, copper, cymoxanil, dichlobutrazole, dichlofluanid, diethofencarb, difenconazole, dimethomorph, diniconazole, dinocap, dithianon, fenarimol, fentin acetate, ferbam, flusilazole, folpet, fosetyl, hexaconazole, imazalil, iprodione, mancopper mancozeb, maneb, mepronil, mercuric oxide, metalaxyl, metiram, myclobutanil, nuarimol, ofurace, oxadixyl, penconazole, pencyuron, phosphorous acid, procymidone, propineb, pyrifenox, quintozene, sodium arsenite, sulphur, thiabendazole, thiophanate methyl, thiram, tolclophosmethyl, triadimefon, triadimenol, triforine, vinclozolin, zineb, and/or ziram.

GENERAL FERMENTATION CONDITIONS

Cultivation of fungal culture 07F275 may be carried out in a wide variety of liquid culture media. Media which are useful for the production of antibiotic include an assimilable source of carbon, such as potato starch, dextrose, maltose, malt extract, etc., an assimilable source of nitrogen such as peptone or potato or malt extract. Inorganic elements are supplied from the complex vegetable or animal extracts used in the media preparation. Aeration is supplied either by agitation in flask or by forcing air through the fermentation. Further agitation is provided by a mechanical impeller. An antifoam agent such as silicon oil may be added as needed.

GENERAL PROCEDURE FOR THE ISOLATION OF 07F725 COMPONENTS

Recovery of the 07F275 antibiotics from fermentations is accomplished by extraction of the whole broth with an organic solvent such as butanol, methylene chloride, ethyl acetate, and butyl acetate, separation of the phases and isolating the 07F275 components from the organic phase.

Alternatively, the 07F275 antibiotics can be obtained from the whole broth by first adding half the fermentation volume of a suitable, water miscible solvent, such as methyl alcohol or acetonitrile, thereafter removing any solid material by filtration, then diluting the obtained filtrate with water to twice its volume and passing the liquid over a resin such as HP-20 or XAD-2 to absorb the 07F275 antibiotics. The 07F275 components are eluted from the resin with an organic solvent, such as methyl alcohol, acetone or acetonitrile. The crude product obtained by the above extractions represents a complex of 07F275 antibiotics from which single compounds can be separated by chromatography. Purification of the individual components is accomplished by a succession of liquid chromatographies on silica gel and/or reverse phase resins with a variety of elution conditions.

The invention will be further described in conjunction with the following non-limiting examples.

EXAMPLE 1

Inoculum Preparation

The culture is maintained on a slant of 3% malt extract agar, prepared by dissolving 30 g of Difco malt extract and 15 g of Difco agar in 1 liter of distilled water and dispensing aliquots into suitable vessels and autoclaving for 20 minutes at 121° C. Following inoculation of the slant, the culture is grown at 22° C. for approximately one week and then stored at room temperature. A plug of this culture is added to a 25×150 mm capped culture tube containing 10 ml of potato dextrose broth, prepared by adding 24 g of Difco dehydrated potato dextrose broth to 1 liter of distilled water which is then autoclaved for 20 minutes at 121° C., and two 6 mm glass beads. This is incubated at 22° C. with shaking at 170 rpm and a two inch throw. After a period, usually between 3–5 days, vigorous growth in the form of black spheres about 2 mm in diameter is observed.

EXAMPLE 2

Fermentation

Two and a half ml of the culture produced in Example 1 is transfered to a 250 ml Erlenmeyer flask containing 50 ml of potato dextrose broth. This is incubated at 22° C. with shaking at 200 rpm with a two inch throw until vigorous growth is observed, which usually is after 3 days of incubation. Two and a half ml of this culture is used to inoculate 250 ml Erlenmeyer flasks containing 50 ml of one of the following media: potato dextrose broth prepared as above; malt extract broth containing 30 g of Difco malt extract per liter of distilled water; Sabouraud maltose medium containing 10 g of Difco neopeptone and 40 g of Bacto maltose per liter of distilled water, and Sabouraud dextrose medium containing 10 g of Difco neopeptone and 40 g of Bacto dextrose per liter of distilled water. These flasks are incubated at 22° C. with shaking at 200 rpm with a two inch throw for 5 to 7 days. All flasks produce activity against various microorganism. Potato dextrose gives the highest level of activity against Gram positive test cultures and against Candida, and the culture is then routinely fermented in this medium.

EXAMPLE 3

One Liter Scale up Fermentation of 07F275

Ten seed tubes are prepared as follows: A plug of culture from a 3% malt extract is added to a 25×150 mm capped culture tube containing 10 ml of potato dextrose broth, prepared as above, and two 6 mm glass beads. These are incubated at 22° C. with shaking at 170 rpm and a two inch throw. After 4 days of incubation, the contents of each tube is used to inoculate individual Erlenmeyer flasks containing 100 ml of potato dextrose medium. These are incubated for 5 days at 22° C. with shaking at 200 rpm with a two inch throw, at which time the fermentation is stopped and provided for chemical evaluation. The following activity is observed:

test culture

S. aureus 310>20 mm;

S. aureus 375>20 mm;

S. aureus 391>25 mm;

E. coli 389 12 mm;

B. subtilis 17 22 mm and

E. coli 300 9 mm.

EXAMPLE 4

300 Liter Scale up of Fermentation of 07F275

Seed medium and Production Medium

Both seed and production media are the same for this culture:

| Ingredients | (%) |
| --- | --- |
| Potato-Dextrose powder | 2.4% |
| DF40-P antifoam | 0.3% |
| Tap water | 1 liter |

S1 Seed Stage 100 ml of seed medium/500 ml flask is inoculated with growth scrappings from Bennetts agar plate growth. The flask is allowed to grow for 4 days at 28° C. in a 170 rpm rotary shaker.

S2 Seed Stage

A 14 liter tank containing 6.0 liters of seed medium is inoculated with 100 ml of S1 seed growth. The tank is allowed to grow out at 22° C. The aeration is set at 6 lpm and the agitation at 200 rpm.

Production Stage

A 410 liter tank containing 300 liters of sterile production medium is inoculated with the contents of the S2 seed tank growth. The temperature is set a 22° C., agitation at 200 rpm, and the air flow is 250 lpm. The back pressure is initially set at 8 psi. The fermentation is allowed to proceed for 6 days after which time it is harvested.

EXAMPLE 5

Isolation and Purification of 07F275alpha, theta, pi, sigma and chi (Flow Chart 1)

To a 300 L culture broth (pH 5.9), fermented for 8 days, is added 3.75 L of toluene and the mixture is stirred for 20 minutes, followed by the addition of 150 L of ethyl acetate. The solution is mixed vigorously for 2 hours, subsequently filtered through a Ceramic Microfilter system, rinsed with 100 L of ethyl acetate and 100 L of water. The filtrate and washes are all combined; the retentate is discarded. The liquid phases are separated and the organic layer is concentrated to a solution weighing 950.3 g which contains 42.2 g of solid material.

The extract is concentrated to approximately 500 ml to which 1500 ml of hexane is added. The mixture is chromatographed on an open silica gel column (1000 g silica gel, 60 Å, 60–300µ: 25% ethyl acetate/hexane). The first 2.25 L (Cuts A–E) of eluent is discarded. The subsequent 500 ml fraction (Cut F) contains the 07F275alpha, theta and sigma.

Two ml of Cut F is chromatographed (silica gel, 2000 µ, 20×20 plates, 5% methyl alcohol/methylene chloride) to give 0.020 g of the three separate components as detected by UV at 254 nm:
07F275alpha, Rf=0.73;
07F275theta, Rf=0.88;
and 07F275sigma, Rf=0.81.

Cut G is used to generate pure 07F275chi. Three reverse phase chromatographies, using each time the MODCol™$C_{18}$ column (100 Å Kromasil $C_{18}$, 10µ2.54×25 cm), are employed to prepare the chi component. For the first two purifications, the column is loaded with 0.220 g of material in 2 ml and is eluted with 42% aqueous methyl alcohol, flow rate 9.9 ml/min. Fractions 4 and 5 of each run (retention time volume 150 ml) are pooled and concentrated to give 0.140 g of a greenish oil. This material is rechromatographed, as above, using 40% aqueous methyl alcohol, flow rate 9.9 ml/min. Concentration of fractions 6 to 9 yields 0.030 g of 07F275chi.

Pure 07F275pi is obtained from Cut H by reverse phase chromatography on a MODCol™$C_{18}$ column (100 Å Kromasil $C_{18}$, 10µ2.54×25 cm). The column is loaded with 0.195 g of material in 2 ml and is eluted with 40% aqueous methyl alcohol, flow rate 9.9 ml/min. Concentration of fractions 9 to 13 (retention volume 320 ml) yields 0.055 g of 07F275pi.

EXAMPLE 6

Isolation and Purification of 07F275beta, zeta, eta, gamma, delta, iota, kappa and epsilon (Flow Chart 2)

A 300 L culture broth, fermented for 4 day, is mixed with 100 L of methyl alcohol for 2 hours and subsequently filtered through diatomaceous earth. The filtrate is applied to a prepared 60-L column filled with XAD-2 resin (300–1000µ), washed with 60 L of 25% methyl alcohol/water, and eluted with increasing concentrations of methyl alcohol (25–100% methyl alcohol/water). The effluent and wash are discarded.

The first eluate, 30–50% methyl alcohol/water, is freeze-dried to yield 22.7 g of solid material, which contained a small amount of an antibiotic, identified as a mycomycin derivative.

The second eluate, 50–80% methyl alcohol/water, is discarded.

The third eluate, 80–100% methyl alcohol/water, is concentrated and freeze-dried from t-butanol solution to give 18.2 g of solid material containing the 07F275 components.

One gram of the freeze-dried material from the 2nd eluate is stirred with 200 ml of methylene chloride, filtered through cotton, and pumped onto a self-packed Michel-Miller HPLPLC column (silica gel; 21–300 mm). An additional 200 ml of methylene chloride is passed through the loaded column before elution of the components is initiated. Elution is accomplished in steps of 300 ml of each of the following solvent compositions: 5%, 10%, 20% and 50% ethyl acetate/methylene chloride. Material with high polarity is washed off the column with 300 ml of methyl alcohol. The flow rate is 4.0 ml/min and the eluate is monitored at 280 nm, using an Isco UV detector. Fractions are collected according to peaks detected, minimun of 3 fractions per peak, the fractions are pooled when appropriate (HPLC analysis).

A total of 24 fraction are obtained, of which the first seven fractions (cut I) are discarded because they contain biologically inactive or non-related material.

Fractions 8–12 (cut II) are combined to give 0.060 g of solid material, which is further purified by chromatography (Whatman CCS/$C_8$ column: 45% methyl alcohol/water) to give 0.006 g of pure 07F275beta.

Fractions 17–23 (cut III) are combined to give 0.465 g of solid material, which is further purified by chromatography (Whatman CCS/$C_8$ column: 30% acetonitrile) to give 0.034 g of pure 07F275eta. A mixture of the zeta and iota component are also obtained from this column. This mixture is rechromatographed (Whatman CCS/$C_8$ column: 45% methyl alcohol/water) to give 0.360 g of 07F275zeta and 0.28 g of 07F275iota.

Fraction 24 (cut IV) contains the 07F275 kappa, delta, gamma and epsilon components. The dried material is dissolved in acetone, filtered and chromatographed (Preparative Silica plates: methylene chloride/methyl alcohol 7/3).

Five UV active zones are detected and extracted with methyl alcohol:

Zone 2 (0.0361 g) contains gamma, delta and epsilon components;

Zone 3 (0.0526 g) contains gamma and kappa components.

These 2 zones are further purified by chromatography (2 preparative HPLC Whatman CCS/$C_8$ column: 45% methyl alcohol/water) to give 0.007 g of gamma, 0.022 g of delta, 0.002g of epsilon and 0.012 g of kappa component. The fractions containing the gamma, delta and kappa components crystallized spontaneously on evaporation.

Flow Chart 1: Isolation of Antibiotics Produced by Culture 07F275
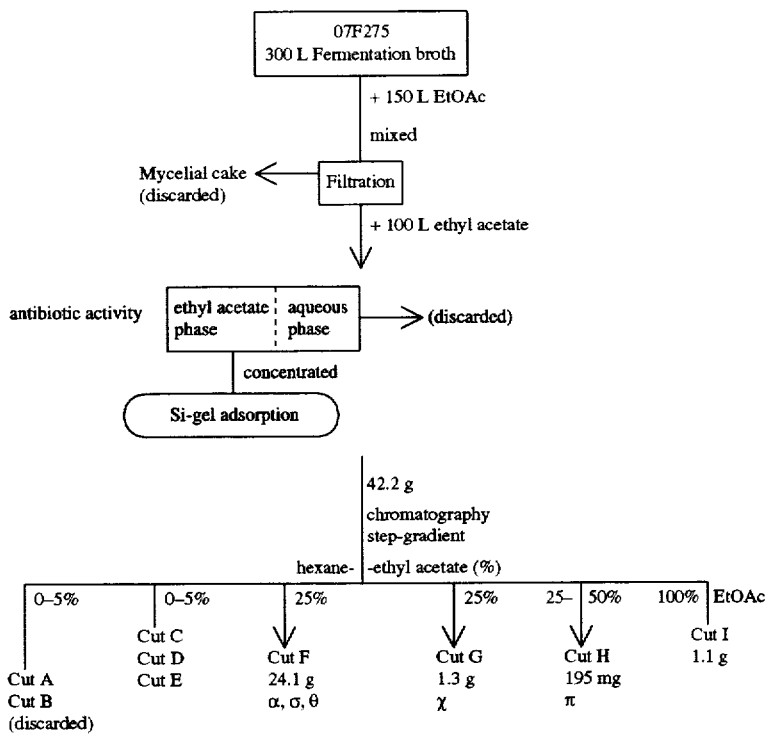
Flow Chart 2: Isolation of Antibiotics Produced by Culture 07F275
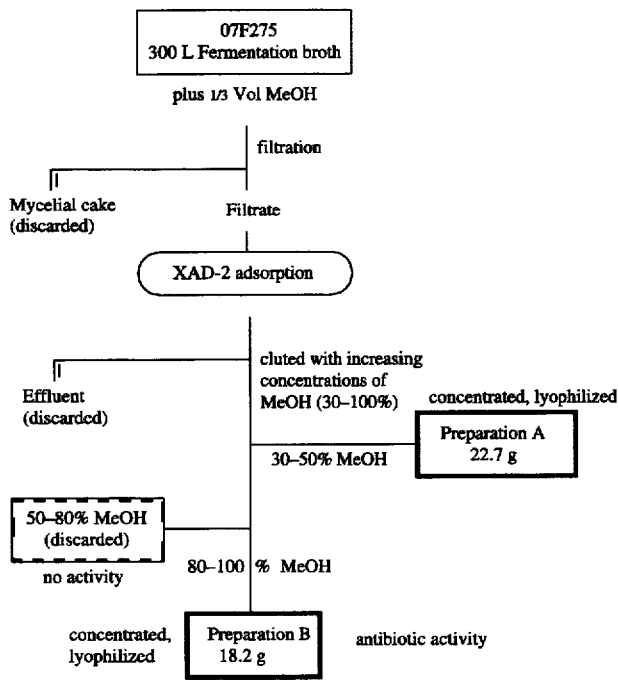

-continued
Flow Chart 2: Isolation of Antibiotics Produced by Culture 07F275
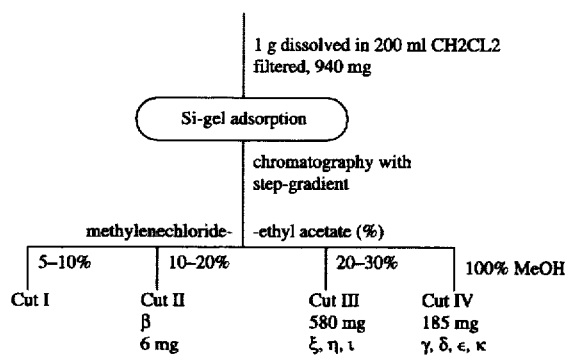
We claim:
1. A compound having the structure:
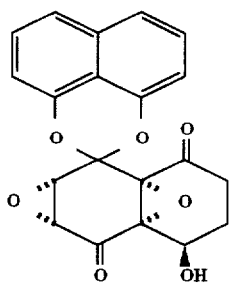
07F275alpha
2. A compound having the structure:
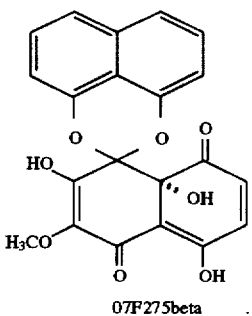
07F275beta
3. A compound having the structure:
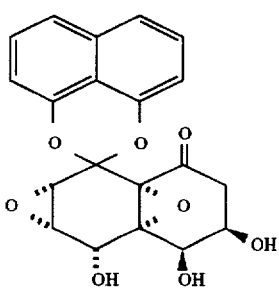
07F275gamma
4. A compound having the structure:
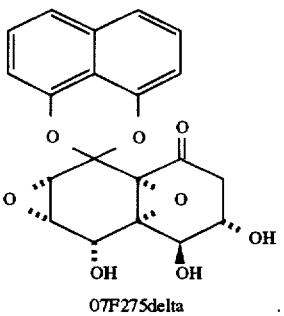
07F275delta
5. A compound having the structure:
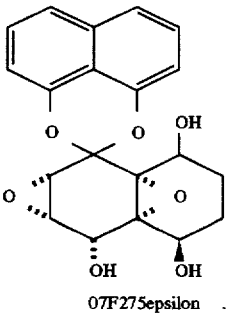
07F275epsilon
6. A compound having the structure:
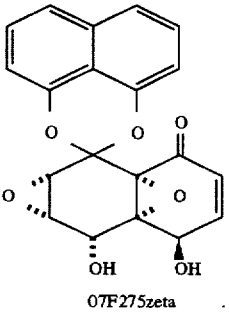
07F275zeta 7. A compound having the structure:
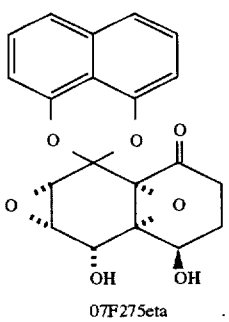
07F275eta
8. A compound having the structure:
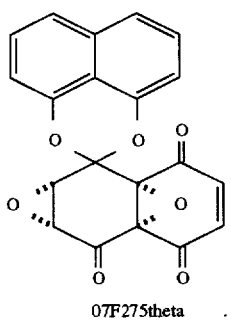
07F275theta
9. A compound having the structure:
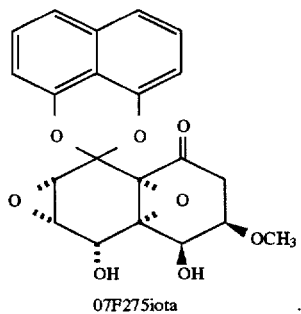
07F275iota
10. A compound having the structure:
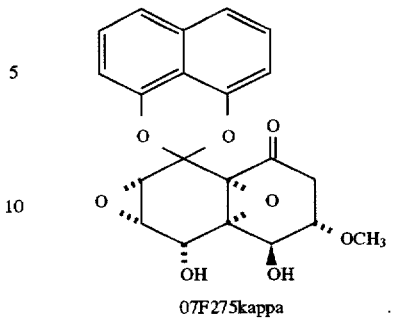
07F275kappa
11. A compound having the structure:
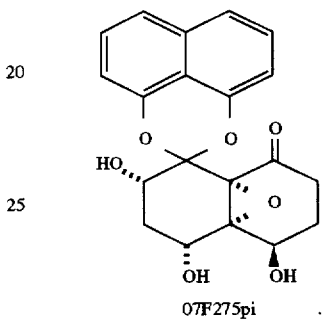
07F275pi
12. A compound having the structure:
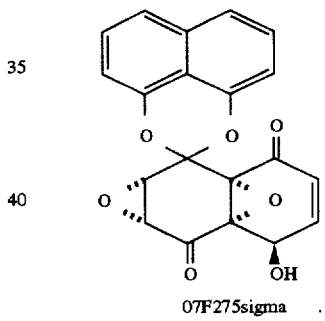
07F275sigma
* * * * *